United States Patent
Palanker

(10) Patent No.: US 9,254,168 B2
(45) Date of Patent: Feb. 9, 2016

(54) ELECTRO-THERMOTHERAPY OF TISSUE USING PENETRATING MICROELECTRODE ARRAY

(75) Inventor: Daniel V. Palanker, Sunnyvale, CA (US)

(73) Assignee: MEDTRONIC ADVANCED ENERGY LLC, Minneapolis, MN (US)

( * ) Notice: Subject to any disclaimer, the term of this patent is extended or adjusted under 35 U.S.C. 154(b) by 1084 days.

(21) Appl. No.: 12/661,443

(22) Filed: Mar. 16, 2010

(65) Prior Publication Data

US 2010/0198216 A1    Aug. 5, 2010

Related U.S. Application Data

(63) Continuation-in-part of application No. 12/657,949, filed on Jan. 29, 2010, now abandoned.

(60) Provisional application No. 61/206,522, filed on Feb. 2, 2009.

(51) Int. Cl.
*A61B 18/14* (2006.01)
*A61B 18/00* (2006.01)

(52) U.S. Cl.
CPC ..... *A61B 18/1477* (2013.01); *A61B 2018/0016* (2013.01); *A61B 2018/00452* (2013.01); *A61B 2018/00589* (2013.01)

(58) Field of Classification Search
CPC .............. A61B 2018/0016; A61B 2018/00452
USPC ............. 606/32, 42, 44, 41; 607/99, 100, 148
See application file for complete search history.

(56) References Cited

U.S. PATENT DOCUMENTS

| | | |
|---|---|---|
| 2,888,928 A | 6/1959 | Seiger |
| 3,682,130 A | 8/1972 | Jeffers |
| 3,750,650 A | 8/1973 | Ruttgers |
| 4,060,088 A | 11/1977 | Morrison, Jr. et al. |
| 4,195,637 A | 4/1980 | Gruntzig et al. |
| 4,207,897 A | 6/1980 | Lloyd et al. |
| 4,244,371 A | 1/1981 | Farin |
| 4,248,224 A | 2/1981 | Jones |
| 4,275,734 A | 6/1981 | Mitchiner |
| 4,276,874 A | 7/1981 | Wolvek et al. |
| 4,278,090 A | 7/1981 | van Gerven |

(Continued)

FOREIGN PATENT DOCUMENTS

| | | |
|---|---|---|
| WO | WO96/04955 A2 | 2/1996 |
| WO | WO2010/141417 | 12/2010 |

OTHER PUBLICATIONS

Hantash et al., "In Vivo Histological Evaluation of a Novel Ablative Fractional Resurfacing Device", 2007, pp. 96-107, Lasers in Surgery and Medicine v39.

*Primary Examiner* — Michael Peffley
*Assistant Examiner* — Thomas Giuliani
(74) *Attorney, Agent, or Firm* — Jeffrey J. Hohenshell

(57) ABSTRACT

Electrosurgical therapy is provided with an electrode array configured to ablate tissue during insertion of the electrode array into tissue being treated. Once the electrode array is fully inserted, deep heating of the treated tissue can be performed by applying an additional waveform to the tissue with the electrode array. Optionally, the electrical waveform can be varied continuously during insertion of the electrode array to control the extent of coagulation at the side walls and at the bottom of the channels produced by tissue ablation.

10 Claims, 4 Drawing Sheets

(56) References Cited

U.S. PATENT DOCUMENTS

| | | |
|---|---|---|
| 4,321,931 A | 3/1982 | Hon |
| 4,342,218 A | 8/1982 | Fox |
| 4,355,642 A | 10/1982 | Alferness |
| 4,377,168 A | 3/1983 | Rzasa et al. |
| 4,381,007 A | 4/1983 | Doss |
| 4,519,389 A | 5/1985 | Gudkin et al. |
| 4,598,698 A | 7/1986 | Siegmund |
| 4,601,290 A | 7/1986 | Effron et al. |
| 4,664,110 A | 5/1987 | Schanzlin |
| 4,671,274 A | 6/1987 | Scrochenko |
| 4,736,749 A | 4/1988 | Lundback |
| 4,779,611 A | 10/1988 | Grooters et al. |
| 4,802,475 A | 2/1989 | Weshahy |
| 4,919,129 A | 4/1990 | Weber et al. |
| 4,931,047 A | 6/1990 | Broadwin et al. |
| 4,932,952 A | 6/1990 | Wojciechowicz, Jr. |
| 4,943,290 A | 7/1990 | Rexroth et al. |
| 4,950,232 A | 8/1990 | Ruzicka et al. |
| 4,985,030 A | 1/1991 | Melzer et al. |
| 4,998,933 A | 3/1991 | Eggers et al. |
| 5,190,541 A | 3/1993 | Abele et al. |
| 5,195,959 A | 3/1993 | Smith |
| 5,234,428 A | 8/1993 | Kaufman |
| 5,254,117 A | 10/1993 | Rigby et al. |
| 5,281,215 A | 1/1994 | Midler |
| 5,309,896 A | 5/1994 | Moll et al. |
| 5,316,000 A | 5/1994 | Chapelon et al. |
| 5,317,878 A | 6/1994 | Bradshaw et al. |
| 5,318,525 A | 6/1994 | West et al. |
| 5,322,520 A | 6/1994 | Milder |
| 5,323,781 A | 6/1994 | Ideker et al. |
| 5,324,255 A | 6/1994 | Passafaro et al. |
| 5,324,284 A | 6/1994 | Imran |
| 5,324,286 A | 6/1994 | Fowler |
| 5,330,521 A | 7/1994 | Cohen |
| 5,334,181 A | 8/1994 | Rubinsky et al. |
| 5,334,193 A | 8/1994 | Nardella |
| 5,336,220 A | 8/1994 | Ryan et al. |
| 5,348,554 A | 9/1994 | Imran et al. |
| 5,353,783 A | 10/1994 | Nakao et al. |
| 5,354,258 A | 10/1994 | Dory |
| 5,361,752 A | 11/1994 | Moll et al. |
| 5,383,874 A | 1/1995 | Jackson et al. |
| 5,385,148 A | 1/1995 | Lesh et al. |
| 5,395,312 A | 3/1995 | Desai |
| 5,396,887 A | 3/1995 | Imran |
| 5,397,304 A | 3/1995 | Truckai |
| 5,400,770 A | 3/1995 | Nakao et al. |
| 5,400,783 A | 3/1995 | Pomeranz et al. |
| 5,401,272 A | 3/1995 | Perkins |
| 5,403,309 A | 4/1995 | Coleman et al. |
| 5,403,311 A | 4/1995 | Abele et al. |
| 5,405,376 A | 4/1995 | Mulier et al. |
| 5,409,483 A | 4/1995 | Campbell et al. |
| 5,417,709 A | 5/1995 | Slater |
| 5,423,807 A | 6/1995 | Mlilder |
| 5,423,811 A | 6/1995 | Imran et al. |
| 5,427,119 A | 6/1995 | Swartz et al. |
| 5,431,168 A | 7/1995 | Webster, Jr. |
| 5,431,649 A | 7/1995 | Mulier et al. |
| 5,433,708 A | 7/1995 | Nichols et al. |
| 5,435,308 A | 7/1995 | Gallup et al. |
| 5,437,651 A | 8/1995 | Todd et al. |
| 5,441,503 A | 8/1995 | Considine et al. |
| 5,443,463 A | 8/1995 | Stern et al. |
| 5,443,470 A | 8/1995 | Stern et al. |
| 5,445,638 A | 8/1995 | Rydell et al. |
| 5,450,843 A | 9/1995 | Moll et al. |
| 5,452,582 A | 9/1995 | Longsworth |
| 5,452,733 A | 9/1995 | Sterman et al. |
| 5,460,629 A | 10/1995 | Shlain et al. |
| 5,462,545 A | 10/1995 | Wang et al. |
| 5,465,717 A | 11/1995 | Imran et al. |
| 5,469,853 A | 11/1995 | Law et al. |
| 5,472,876 A | 12/1995 | Fahy |
| 5,478,309 A | 12/1995 | Sweezer et al. |
| 5,478,330 A | 12/1995 | Imran et al. |
| 5,486,193 A | 1/1996 | Bourne et al. |
| 5,487,385 A | 1/1996 | Avitall |
| 5,487,757 A | 1/1996 | Truckai et al. |
| 5,490,819 A | 2/1996 | Nicholas et al. |
| 5,496,271 A | 3/1996 | Burton et al. |
| 5,496,312 A | 3/1996 | Klicek |
| 5,497,774 A | 3/1996 | Swartz et al. |
| 5,498,248 A | 3/1996 | Milder |
| 5,500,012 A | 3/1996 | Brucker et al. |
| 5,505,700 A | 4/1996 | Leone |
| 5,505,730 A | 4/1996 | Edwards |
| 5,516,505 A | 5/1996 | McDow |
| 5,520,682 A | 5/1996 | Baust et al. |
| 5,522,870 A | 6/1996 | Ben-Zion |
| 5,536,267 A | 7/1996 | Edwards et al. |
| 5,540,562 A | 7/1996 | Giter |
| 5,542,916 A | 8/1996 | Hirsch et al. |
| 5,542,945 A | 8/1996 | Fritzsch |
| 5,545,195 A | 8/1996 | Lennox et al. |
| 5,545,200 A | 8/1996 | West et al. |
| 5,549,661 A | 8/1996 | Kordis et al. |
| 5,555,883 A | 9/1996 | Avitall |
| 5,556,397 A | 9/1996 | Long et al. |
| 5,558,671 A | 9/1996 | Yates |
| 5,560,362 A | 10/1996 | Silwa, Jr. et al. |
| 5,562,702 A | 10/1996 | Huitema et al. |
| 5,562,720 A | 10/1996 | Stern et al. |
| 5,569,241 A | 10/1996 | Edwards |
| 5,569,243 A | 10/1996 | Kortenbach et al. |
| 5,571,088 A | 11/1996 | Lennox et al. |
| 5,571,215 A | 11/1996 | Sterman et al. |
| 5,573,424 A | 11/1996 | Poppe |
| 5,573,532 A | 11/1996 | Chang et al. |
| 5,575,766 A | 11/1996 | Swartz et al. |
| 5,575,788 A | 11/1996 | Baker et al. |
| 5,575,810 A | 11/1996 | Swanson et al. |
| 5,578,007 A | 11/1996 | Imran |
| 5,582,609 A | 12/1996 | Swanson et al. |
| 5,588,432 A | 12/1996 | Crowley |
| 5,590,657 A | 1/1997 | Cain et al. |
| 5,595,183 A | 1/1997 | Swanson et al. |
| 5,599,346 A | 2/1997 | Edwards et al. |
| 5,605,539 A | 2/1997 | Buelna et al. |
| 5,607,462 A | 3/1997 | Imran |
| 5,617,854 A | 4/1997 | Munsif |
| 5,630,837 A | 5/1997 | Crowley |
| 5,637,090 A | 6/1997 | McGee et al. |
| 5,643,197 A | 7/1997 | Brucker et al. |
| 5,647,869 A | 7/1997 | Goble et al. |
| 5,656,029 A | 8/1997 | Imran et al. |
| 5,658,278 A | 8/1997 | Imran et al. |
| 5,671,747 A | 9/1997 | Connor |
| 5,673,695 A | 10/1997 | McGee et al. |
| 5,676,662 A | 10/1997 | Fleischhacker et al. |
| 5,676,692 A | 10/1997 | Sanghvi et al. |
| 5,676,693 A | 10/1997 | Lafontaine |
| 5,678,550 A | 10/1997 | Bassen et al. |
| 5,680,860 A | 10/1997 | Imran |
| 5,681,278 A | 10/1997 | Igo et al. |
| 5,681,294 A | 10/1997 | Osborne et al. |
| 5,681,308 A | 10/1997 | Edwards et al. |
| 5,687,723 A | 11/1997 | Avitall |
| 5,687,737 A | 11/1997 | Branham et al. |
| 5,688,267 A | 11/1997 | Panescu et al. |
| 5,690,611 A | 11/1997 | Swartz et al. |
| 5,697,536 A | 12/1997 | Eggers et al. |
| 5,697,882 A | 12/1997 | Eggers et al. |
| 5,697,925 A | 12/1997 | Taylor |
| 5,697,927 A | 12/1997 | Imran et al. |
| 5,697,928 A | 12/1997 | Walcott et al. |
| 5,713,942 A | 2/1998 | Stern |
| 5,716,389 A | 2/1998 | Walinsky et al. |
| 5,718,241 A | 2/1998 | Ben-Haim et al. |
| 5,718,701 A | 2/1998 | Shai et al. |
| 5,720,775 A | 2/1998 | Larnard |
| 5,722,402 A | 3/1998 | Swanson et al. |
| 5,730,074 A | 3/1998 | Peter |

(56) References Cited

U.S. PATENT DOCUMENTS

| | | |
|---|---|---|
| 5,730,127 A | 3/1998 | Avitall |
| 5,730,704 A | 3/1998 | Avitall |
| 5,733,280 A | 3/1998 | Avitall |
| 5,735,280 A | 4/1998 | Sherman et al. |
| 5,743,903 A | 4/1998 | Stern et al. |
| 5,755,760 A | 5/1998 | Maguire et al. |
| 5,766,167 A | 6/1998 | Eggers et al. |
| 5,769,846 A | 6/1998 | Edwards et al. |
| 5,782,828 A | 7/1998 | Chen et al. |
| 5,785,706 A | 7/1998 | Bednarek |
| 5,788,636 A | 8/1998 | Curley |
| 5,792,140 A | 8/1998 | Tu et al. |
| 5,797,905 A | 8/1998 | Fleischman et al. |
| 5,797,960 A | 8/1998 | Stevens et al. |
| 5,800,428 A | 9/1998 | Nelson et al. |
| 5,800,482 A | 9/1998 | Pomeranz et al. |
| 5,810,764 A | 9/1998 | Eggers et al. |
| 5,810,802 A | 9/1998 | Panescu et al. |
| 5,814,040 A | 9/1998 | Nelson et al. |
| 5,827,216 A | 10/1998 | Igo et al. |
| 5,836,947 A | 11/1998 | Fleischman et al. |
| 5,840,030 A | 11/1998 | Ferek-Petric et al. |
| 5,843,021 A | 12/1998 | Edwards et al. |
| 5,843,152 A | 12/1998 | Tu et al. |
| 5,844,349 A | 12/1998 | Oakley et al. |
| 5,846,187 A | 12/1998 | Wells et al. |
| 5,846,191 A | 12/1998 | Wells et al. |
| 5,849,028 A | 12/1998 | Chen |
| 5,861,021 A | 1/1999 | Thome et al. |
| 5,871,523 A | 2/1999 | Fleischman et al. |
| 5,871,524 A | 2/1999 | Knowlton |
| 5,871,525 A | 2/1999 | Edwards et al. |
| 5,873,845 A | 2/1999 | Cline et al. |
| 5,873,855 A | 2/1999 | Eggers et al. |
| 5,876,399 A | 3/1999 | Chia et al. |
| 5,879,295 A | 3/1999 | Li et al. |
| 5,879,296 A | 3/1999 | Ockuly et al. |
| 5,879,348 A | 3/1999 | Owens et al. |
| 5,881,732 A | 3/1999 | Sung et al. |
| 5,882,346 A | 3/1999 | Pomeranz et al. |
| 5,885,278 A | 3/1999 | Fleischman |
| 5,891,142 A | 4/1999 | Eggers et al. |
| 5,893,848 A | 4/1999 | Negus et al. |
| 5,895,355 A | 4/1999 | Schaer |
| 5,895,417 A | 4/1999 | Pomeranz et al. |
| 5,897,553 A | 4/1999 | Mulier et al. |
| 5,897,554 A | 4/1999 | Chia et al. |
| 5,899,898 A | 5/1999 | Arless et al. |
| 5,899,899 A | 5/1999 | Arless et al. |
| 5,902,289 A | 5/1999 | Swartz et al. |
| 5,904,711 A | 5/1999 | Flom et al. |
| 5,906,580 A | 5/1999 | Kline-Schoder et al. |
| 5,906,587 A | 5/1999 | Zimmon |
| 5,906,606 A | 5/1999 | Chee et al. |
| 5,908,029 A | 6/1999 | Knudson et al. |
| 5,913,854 A | 6/1999 | Maguire et al. |
| 5,916,213 A | 6/1999 | Haissaguerre et al. |
| 5,916,214 A | 6/1999 | Cosio et al. |
| 5,921,924 A | 7/1999 | Avitall |
| 5,921,982 A | 7/1999 | Lesh et al. |
| 5,925,045 A | 7/1999 | Reimels et al. |
| 5,927,284 A | 7/1999 | Borst et al. |
| 5,928,191 A | 7/1999 | Houser et al. |
| 5,931,810 A | 8/1999 | Grabek |
| 5,931,848 A | 8/1999 | Saadat |
| 5,935,123 A | 8/1999 | Edwards et al. |
| 5,944,715 A | 8/1999 | Goble et al. |
| 5,954,661 A | 9/1999 | Greenspon et al. |
| 5,957,919 A | 9/1999 | Laufer |
| 5,971,980 A | 10/1999 | Sherman |
| 5,971,983 A | 10/1999 | Lesh |
| 5,980,516 A | 11/1999 | Mulier et al. |
| 5,989,248 A | 11/1999 | Tu et al. |
| 5,993,412 A | 11/1999 | Deily et al. |
| 5,993,447 A | 11/1999 | Blewett et al. |
| 6,004,316 A | 12/1999 | Laufer |
| 6,004,319 A | 12/1999 | Goble et al. |
| 6,007,499 A | 12/1999 | Martin et al. |
| 6,010,500 A | 1/2000 | Sherman et al. |
| 6,012,457 A | 1/2000 | Lesh |
| 6,015,391 A | 1/2000 | Rishton et al. |
| 6,016,811 A | 1/2000 | Knopp et al. |
| 6,018,676 A | 1/2000 | Davis et al. |
| 6,019,757 A | 2/2000 | Scheldrup |
| 6,024,733 A | 2/2000 | Eggers et al. |
| 6,030,381 A | 2/2000 | Jones et al. |
| 6,036,687 A | 3/2000 | Laufer et al. |
| 6,042,556 A | 3/2000 | Beach et al. |
| 6,048,333 A | 4/2000 | Lennox et al. |
| 6,056,744 A | 5/2000 | Edwards |
| 6,056,745 A | 5/2000 | Panescu et al. |
| 6,056,746 A | 5/2000 | Goble |
| 6,056,747 A | 5/2000 | Saadat et al. |
| 6,063,081 A | 5/2000 | Mulier |
| 6,066,139 A | 5/2000 | Ryan et al. |
| 6,068,653 A | 5/2000 | LaFontaine |
| 6,071,279 A | 6/2000 | Whayne et al. |
| 6,083,237 A | 7/2000 | Huitema et al. |
| 6,086,585 A | 7/2000 | Hovda et al. |
| 6,088,894 A | 7/2000 | Oakley |
| 6,096,037 A | 8/2000 | Mulier |
| 6,113,592 A | 9/2000 | Taylor |
| 6,113,596 A | 9/2000 | Hooven et al. |
| 6,117,101 A | 9/2000 | Diederich et al. |
| 6,120,496 A | 9/2000 | Whayne et al. |
| 6,141,576 A | 10/2000 | Littmann et al. |
| 6,142,993 A | 11/2000 | Whayne et al. |
| 6,142,994 A | 11/2000 | Swanson et al. |
| 6,149,620 A | 11/2000 | Baker et al. |
| 6,152,920 A | 11/2000 | Thompson et al. |
| 6,161,543 A | 12/2000 | Cox et al. |
| 6,165,174 A | 12/2000 | Jacobs et al. |
| 6,190,384 B1 | 2/2001 | Ouchi |
| 6,193,716 B1 | 2/2001 | Shannon, Jr. |
| 6,210,406 B1 | 4/2001 | Webster |
| 6,210,410 B1 | 4/2001 | Farin et al. |
| 6,210,411 B1 | 4/2001 | Hofmann et al. |
| 6,212,426 B1 | 4/2001 | Swanson |
| 6,216,704 B1 | 4/2001 | Ingle et al. |
| 6,217,528 B1 | 4/2001 | Koblish et al. |
| 6,217,576 B1 | 4/2001 | Tu et al. |
| 6,224,592 B1 | 5/2001 | Eggers et al. |
| 6,231,518 B1 | 5/2001 | Grabek et al. |
| 6,231,591 B1 | 5/2001 | Desai |
| 6,235,020 B1 | 5/2001 | Cheng et al. |
| 6,235,024 B1 | 5/2001 | Tu |
| 6,237,605 B1 | 5/2001 | Vaska et al. |
| 6,238,347 B1 | 5/2001 | Nix et al. |
| 6,238,387 B1 | 5/2001 | Miller, III |
| 6,238,393 B1 | 5/2001 | Mulier |
| 6,245,061 B1 | 6/2001 | Panescu et al. |
| 6,245,064 B1 | 6/2001 | Lesh et al. |
| 6,245,065 B1 | 6/2001 | Panescu et al. |
| 6,251,092 B1 | 6/2001 | Qin et al. |
| 6,251,110 B1 | 6/2001 | Wampler |
| 6,251,128 B1 | 6/2001 | Knopp et al. |
| 6,258,087 B1 | 7/2001 | Edwards et al. |
| 6,264,650 B1 | 7/2001 | Hovda et al. |
| 6,266,551 B1 | 7/2001 | Osadchy et al. |
| 6,270,471 B1 | 8/2001 | Hechel et al. |
| 6,277,116 B1 * | 8/2001 | Utely ............... A61B 18/14 606/41 |
| 6,283,988 B1 | 9/2001 | Laufer et al. |
| 6,283,989 B1 | 9/2001 | Laufer et al. |
| 6,293,943 B1 | 9/2001 | Panescu et al. |
| 6,296,619 B1 | 10/2001 | Brisken et al. |
| 6,299,633 B1 | 10/2001 | Laufer |
| 6,302,880 B1 | 10/2001 | Schaer |
| 6,311,692 B1 | 11/2001 | Vaska et al. |
| 6,312,383 B1 | 11/2001 | Lizzi et al. |
| 6,314,962 B1 | 11/2001 | Vaska et al. |
| 6,314,963 B1 | 11/2001 | Vaska et al. |
| 6,322,559 B1 | 11/2001 | Daulton et al. |
| 6,325,797 B1 | 12/2001 | Stewart et al. |

(56) References Cited

U.S. PATENT DOCUMENTS

| | | |
|---|---|---|
| 6,328,735 B1 | 12/2001 | Curley et al. |
| 6,328,736 B1 | 12/2001 | Mulier |
| 6,332,881 B1 | 12/2001 | Carner et al. |
| 6,352,533 B1 | 3/2002 | Ellman et al. |
| 6,358,248 B1 | 3/2002 | Mulier |
| 6,361,531 B1 | 3/2002 | Hissong |
| 6,364,876 B1 | 4/2002 | Erb et al. |
| 6,368,275 B1 | 4/2002 | Sliwa et al. |
| 6,371,955 B1 | 4/2002 | Fuimaono et al. |
| 6,371,956 B1 | 4/2002 | Wilson et al. |
| 6,383,151 B1 | 5/2002 | Diederich et al. |
| 6,385,472 B1 | 5/2002 | Hall et al. |
| 6,398,792 B1 | 6/2002 | O'Connor |
| 6,409,722 B1 | 6/2002 | Hoey |
| 6,413,254 B1 | 7/2002 | Hissong et al. |
| 6,416,509 B1 | 7/2002 | Goble et al. |
| 6,419,648 B1 | 7/2002 | Vitek et al. |
| 6,425,867 B1 | 7/2002 | Vaezy et al. |
| 6,430,426 B2 | 8/2002 | Avitall |
| 6,440,130 B1 | 8/2002 | Mulier |
| 6,443,952 B1 | 9/2002 | Mulier |
| 6,447,507 B1 | 9/2002 | Bednarek et al. |
| 6,461,314 B1 | 10/2002 | Pant et al. |
| 6,461,356 B1 | 10/2002 | Patterson |
| 6,464,700 B1 | 10/2002 | Koblish et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B2 | 11/2002 | Mulier |
| 6,477,396 B1 | 11/2002 | Mest et al. |
| 6,478,793 B1 | 11/2002 | Cosman et al. |
| 6,484,727 B1 | 11/2002 | Vaska et al. |
| 6,488,678 B2 | 12/2002 | Sherman |
| 6,488,680 B1 | 12/2002 | Francischelli |
| 6,497,704 B2 | 12/2002 | Ein-Gal |
| 6,502,575 B2 | 1/2003 | Jacobs et al. |
| 6,508,815 B1 | 1/2003 | Strul et al. |
| 6,514,250 B1 | 2/2003 | Jahns |
| 6,517,536 B2 | 2/2003 | Hooven et al. |
| 6,527,767 B2 | 3/2003 | Wang et al. |
| 6,537,248 B2 | 3/2003 | Mulier |
| 6,537,272 B2 | 3/2003 | Christopherson et al. |
| 6,558,382 B2 | 5/2003 | Jahns |
| 6,558,385 B1 | 5/2003 | McClurken et al. |
| 5,697,536 C1 | 6/2003 | Eggers et al. |
| 6,575,969 B1 | 6/2003 | Rittman, III et al. |
| 6,579,288 B1 | 6/2003 | Swanson et al. |
| 6,584,360 B2 | 6/2003 | Francischelli |
| 6,585,732 B2 | 7/2003 | Mulier |
| 6,602,248 B1 | 8/2003 | Sharps et al. |
| 6,603,988 B2 | 8/2003 | Dowlatshahi |
| 6,605,084 B2 | 8/2003 | Acker et al. |
| 6,610,055 B1 | 8/2003 | Swanson et al. |
| 6,610,060 B2 | 8/2003 | Mulier |
| 6,613,048 B2 | 9/2003 | Mulier |
| 6,635,034 B1 | 10/2003 | Cosmescu |
| 6,645,199 B1 | 11/2003 | Jenkins et al. |
| 6,645,202 B1 | 11/2003 | Pless et al. |
| 6,648,883 B2 | 11/2003 | Francischelli |
| 6,656,175 B2 | 12/2003 | Francischelli |
| 6,662,054 B2 | 12/2003 | Kreindel et al. |
| 6,663,627 B2 | 12/2003 | Francischelli |
| 6,666,862 B2 | 12/2003 | Jain et al. |
| 6,679,882 B1 | 1/2004 | Kornerup |
| 6,682,501 B1 | 1/2004 | Nelson |
| 6,689,131 B2 | 2/2004 | McClurken |
| 6,692,450 B1 | 2/2004 | Coleman |
| 6,699,240 B2 | 3/2004 | Francischelli |
| 6,702,810 B2 | 3/2004 | McClurken et al. |
| 6,702,811 B2 | 3/2004 | Stewart et al. |
| 6,706,038 B2 | 3/2004 | Francischelli |
| 6,706,039 B2 | 3/2004 | Mulier |
| 6,716,211 B2 | 4/2004 | Mulier |
| 6,723,090 B2 | 4/2004 | Altshuler et al. |
| 6,736,810 B2 | 5/2004 | Hoey |
| 6,755,827 B2 | 6/2004 | Mulier |
| 6,764,487 B2 | 7/2004 | Mulier |
| 6,766,202 B2 | 7/2004 | Underwood et al. |
| 6,766,817 B2 | 7/2004 | da Silva |
| 6,773,433 B2 | 8/2004 | Stewart et al. |
| 6,775,575 B2 | 8/2004 | Bommannan et al. |
| 6,776,780 B2 | 8/2004 | Mulier |
| 6,786,906 B1 | 9/2004 | Cobb |
| 6,807,968 B2 | 10/2004 | Francischelli |
| 6,827,713 B2 | 12/2004 | Bek et al. |
| 6,827,715 B2 | 12/2004 | Francischelli |
| 6,832,996 B2 | 12/2004 | Woloszko et al. |
| 6,849,073 B2 | 2/2005 | Hoey |
| 6,858,028 B2 | 2/2005 | Mulier |
| 6,887,238 B2 | 5/2005 | Jahns |
| 6,899,711 B2 | 5/2005 | Stewart et al. |
| 6,911,019 B2 | 6/2005 | Mulier |
| 6,915,806 B2 | 7/2005 | Pacek et al. |
| 6,916,318 B2 | 7/2005 | Francischelli |
| 6,918,404 B2 | 7/2005 | Dias da Silva |
| 6,936,046 B2 | 8/2005 | Hissong |
| 6,942,661 B2 | 9/2005 | Swanson |
| 6,949,097 B2 | 9/2005 | Stewart et al. |
| 6,949,098 B2 | 9/2005 | Mulier |
| 6,953,461 B2 | 10/2005 | McClurken et al. |
| 6,960,205 B2 | 11/2005 | Jahns |
| 6,962,589 B2 | 11/2005 | Mulier |
| 7,066,586 B2 | 6/2006 | da Silva |
| 7,156,845 B2 | 1/2007 | Mulier et al. |
| 7,166,106 B2 | 1/2007 | Bartel et al. |
| 7,207,471 B2 | 4/2007 | Heinrich et al. |
| 7,232,440 B2 | 6/2007 | Dumbauld et al. |
| 7,247,155 B2 | 7/2007 | Hoey et al. |
| 7,261,711 B2 | 8/2007 | Mulier et al. |
| 7,309,325 B2 | 12/2007 | Mulier et al. |
| 7,311,708 B2 | 12/2007 | McClurken |
| 7,322,974 B2 | 1/2008 | Swoyer et al. |
| 7,361,175 B2 | 4/2008 | Suslov |
| 7,364,579 B2 | 4/2008 | Mulier et al. |
| 7,537,595 B2 | 5/2009 | McClurken |
| 7,604,635 B2 | 10/2009 | McClurken et al. |
| 7,608,072 B2 | 10/2009 | Swanson |
| 7,645,277 B2 | 1/2010 | McClurken et al. |
| 7,651,494 B2 | 1/2010 | McClurken et al. |
| 7,691,050 B2 | 4/2010 | Gellman |
| 7,708,733 B2 * | 5/2010 | Sanders ............ A61B 18/1402 606/32 |
| 7,736,361 B2 | 6/2010 | Palanker |
| 7,811,282 B2 | 10/2010 | McClurken |
| 7,815,634 B2 | 10/2010 | McClurken et al. |
| 7,909,820 B2 | 3/2011 | Lipson |
| 7,942,872 B2 | 5/2011 | Ein-Gal |
| 7,976,544 B2 | 7/2011 | McClurken |
| 7,993,337 B2 | 8/2011 | Lesh |
| 7,997,278 B2 | 8/2011 | Utley et al. |
| 7,998,140 B2 | 8/2011 | McClurken |
| 8,034,071 B2 | 10/2011 | Scribner et al. |
| 8,038,670 B2 | 10/2011 | McClurken |
| 8,048,070 B2 | 11/2011 | O'Brien |
| 8,083,736 B2 | 12/2011 | Mcclurken et al. |
| 8,105,323 B2 | 1/2012 | Buysse et al. |
| 8,172,828 B2 | 5/2012 | Chang et al. |
| 8,177,783 B2 | 5/2012 | Davison et al. |
| 8,216,233 B2 | 7/2012 | McClurken |
| 8,348,946 B2 | 1/2013 | McClurken |
| 8,361,068 B2 | 1/2013 | McClurken |
| 8,388,642 B2 | 3/2013 | Muni et al. |
| 2001/0020167 A1* | 9/2001 | Woloszko .......... A61B 18/1402 606/45 |
| 2002/0049483 A1 | 4/2002 | Knowlton |
| 2002/0062131 A1 | 5/2002 | Gallo, Sr. |
| 2002/0082643 A1 | 6/2002 | Milla et al. |
| 2002/0120261 A1* | 8/2002 | Morris ............... A61B 18/1477 606/41 |
| 2003/0014050 A1 | 1/2003 | Sharkey et al. |
| 2003/0032954 A1 | 2/2003 | Carranza et al. |
| 2003/0045872 A1 | 3/2003 | Jacobs |
| 2003/0073993 A1 | 4/2003 | Ciarrocca |
| 2003/0144656 A1 | 7/2003 | Ocel |

(56) References Cited

U.S. PATENT DOCUMENTS

| | | |
|---|---|---|
| 2003/0191462 A1 | 10/2003 | Jacobs |
| 2003/0204185 A1 | 10/2003 | Sherman et al. |
| 2003/0216724 A1 | 11/2003 | Jahns |
| 2004/0015106 A1 | 1/2004 | Coleman |
| 2004/0015219 A1 | 1/2004 | Francischelli |
| 2004/0024395 A1 | 2/2004 | Ellman et al. |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0111136 A1 | 6/2004 | Sharkey et al. |
| 2004/0111137 A1 | 6/2004 | Sharkey et al. |
| 2004/0116923 A1 | 6/2004 | Desinger |
| 2004/0138621 A1 | 7/2004 | Jahns |
| 2004/0138656 A1 | 7/2004 | Francischelli |
| 2004/0143260 A1 | 7/2004 | Francischelli |
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0267326 A1 | 12/2004 | Ocel |
| 2005/0010095 A1 | 1/2005 | Stewart et al. |
| 2005/0033280 A1 | 2/2005 | Francischelli |
| 2005/0090815 A1 | 4/2005 | Francischelli |
| 2005/0090816 A1 | 4/2005 | McClurken et al. |
| 2005/0143729 A1 | 6/2005 | Francischelli |
| 2005/0165392 A1 | 7/2005 | Francischelli |
| 2005/0171525 A1 | 8/2005 | Rioux |
| 2005/0209564 A1 | 9/2005 | Bonner |
| 2005/0222565 A1 * | 10/2005 | Manstein ............ A61B 18/1477 606/41 |
| 2005/0267454 A1 | 12/2005 | Hissong |
| 2006/0009756 A1 | 1/2006 | Francischelli |
| 2006/0009759 A1 | 1/2006 | Christian |
| 2006/0047281 A1 * | 3/2006 | Kreindel ................ A61B 18/14 606/49 |
| 2006/0064085 A1 | 3/2006 | Schechter et al. |
| 2006/0106375 A1 | 5/2006 | Werneth et al. |
| 2007/0049920 A1 | 3/2007 | McClurken et al. |
| 2007/0093808 A1 | 4/2007 | Mulier et al. |
| 2007/0118114 A1 | 5/2007 | Miller et al. |
| 2007/0142885 A1 | 6/2007 | Hantash et al. |
| 2007/0149965 A1 | 6/2007 | Gallo, Sr. et al. |
| 2007/0208332 A1 | 9/2007 | Mulier et al. |
| 2008/0004656 A1 | 1/2008 | Livneh |
| 2008/0015563 A1 | 1/2008 | Hoey et al. |
| 2008/0058796 A1 | 3/2008 | O'Brien et al. |
| 2008/0071270 A1 | 3/2008 | Desinger et al. |
| 2008/0091182 A1 | 4/2008 | Mehta |
| 2008/0103494 A1 | 5/2008 | Rioux |
| 2008/0207028 A1 | 8/2008 | Schutz |
| 2008/0262489 A1 | 10/2008 | Steinke |
| 2009/0264879 A1 | 10/2009 | McClurken et al. |
| 2009/0306655 A1 | 12/2009 | Stangeness |
| 2010/0069904 A1 | 3/2010 | Cunningham |
| 2010/0100095 A1 | 4/2010 | McClurken et al. |
| 2010/0160906 A1 | 6/2010 | Jarrard |
| 2010/0168743 A1 | 7/2010 | Stone et al. |
| 2010/0204560 A1 | 8/2010 | Salahieh et al. |
| 2010/0241178 A1 | 9/2010 | Tilson et al. |
| 2011/0028965 A1 | 2/2011 | McClurken |
| 2011/0137298 A1 | 6/2011 | Nguyen et al. |
| 2011/0178515 A1 | 7/2011 | Bloom et al. |
| 2011/0196367 A1 | 8/2011 | Gallo |
| 2011/0295249 A1 | 12/2011 | Bloom et al. |
| 2011/0319889 A1 | 12/2011 | Conley et al. |
| 2012/0004657 A1 | 1/2012 | Conley et al. |
| 2012/0071712 A1 | 3/2012 | Manwaring et al. |
| 2012/0095461 A1 | 4/2012 | Herscher et al. |
| 2012/0101496 A1 | 4/2012 | McClurken et al. |
| 2012/0116397 A1 | 5/2012 | Rencher et al. |
| 2012/0143293 A1 | 6/2012 | Mauch et al. |
| 2012/0150165 A1 | 6/2012 | Conley et al. |
| 2012/0157989 A1 | 6/2012 | Stone et al. |
| 2012/0184983 A1 | 7/2012 | Chang et al. |
| 2012/0191084 A1 | 7/2012 | Davison et al. |
| 2012/0253343 A1 | 10/2012 | McClurken et al. |

* cited by examiner

ELECTRO-THERMOTHERAPY OF TISSUE USING PENETRATING MICROELECTRODE ARRAY

CROSS REFERENCE TO RELATED APPLICATIONS

This application is a continuation in part of U.S. application Ser. No. 12/657,949, entitled "Electro-thermotherapy of tissue using penetrating microelectrode array", filed Jan. 29, 2010, now abandoned, and hereby incorporated by reference in its entirety. Application Ser. No. 12/657,949 claims the benefit of U.S. provisional application 61/206,522, entitled "Electro-thermotherapy of tissue using penetrating microelectrode array", filed Feb. 2, 2009, and hereby incorporated by reference in its entirety.

FIELD OF THE INVENTION

This invention is in the general field of electrosurgery. One application is to electrosurgery for cosmetic procedures on skin.

BACKGROUND

Various approaches have been considered for skin rejuvenation and other tissue/skin treatments based on delivery of energy to the tissue being treated. In non-ablative approaches, energy is delivered to tissue, but no tissue is thereby removed. In ablative approaches, energy is delivered to tissue such that some of the tissue is removed by ablation.

Non-ablative skin rejuvenation (e.g., using radiofrequency, ultrasound, or light) is typically performed using application of the electrical current, ultrasound energy or light beam to the tissue surface, and heating tissue to temperatures not exceeding the vaporization threshold. Optical examples of this approach include U.S. Pat. No. 6,723,090. Electrical examples of this approach include U.S. Pat. Nos. 5,871,524; 6,662,054.

Carbon dioxide ($CO_2$) laser systems have been recently applied to ablative fractional resurfacing of human skin. In these procedures, a pulsed $CO_2$ laser is used to drill channels of approximately 100 micrometers in diameter and 0.5-0.7 mm in depth. Using scanning mirror, these holes are applied in patterns with spacing of approximately 1 mm. The epidermis and part of the dermis demonstrate columns of thermal coagulation that surround tapering ablative zones lined by a thin eschar layer. Typically, a thermal coagulation zone at the edges of such laser channels in skin is on the order of 40 micrometers. Such ablation (tissue removal) and coagulation of skin leads to stimulation of its rejuvenation and tightening, and thus results in improved cosmetic appearance. This approach, called "fractional skin resurfacing" was found to be clinically very effective. An example of this approach is considered by Hantash et al. in an article titled "In vivo Histological Evaluation of a Novel Ablative Fractional Resurfacing Device" (Lasers in Surgery and Medicine 39:96-107 (2007)).

Disadvantages of the $CO_2$ laser systems include their relatively large size, somewhat cumbersome articulated arm beam delivery system, and relatively high cost. In addition, since ablation craters produced by lasers taper towards the bottom, there is a limit on the ratio of depth-to-width of the channels (so called aspect ratio) that can be produced by laser ablation. Typically this aspect ratio does not exceed 10, i.e. channels of 100 µm in diameter do not exceed 1 mm in depth. Another limitation of the laser-based tissue drilling approach is that the thermal damage zone at the side walls of the channels is typically similar or even larger than that at the bottom.

Another non-ablative approach that has been considered for such skin treatment is the use of an array of needle electrodes that is first inserted into the skin, and then energized to provide therapeutic effects. Examples of this approach include US 2007/0142885 and US 2008/0091182. However, insertion of the needles and following tissue coagulation in this approach does not involve tissue removal by ablation (vaporization and ejection forming the empty channels or craters), and thus is not as effective in skin tightening as the ablative laser approach.

It would be desirable to be able to ablate tissue and create channels of arbitrary aspect ratio and with an independent control over the width of the thermal damage zone at the side walls and at the bottom.

SUMMARY

Electrosurgical therapy is provided with an electrode array configured to ablate tissue during insertion of the electrode array into tissue being treated, and to form coagulation zone at the edges of the channels. Once the electrode array is fully inserted, deep heating of the treated tissue can be performed by applying an additional waveform to the tissue with the electrode array. Optionally, the electrical waveform can be varied continuously during insertion of the electrode array for balancing both functions—ablation and coagulation at various depths of the channels.

Compared to laser treatment approaches and mechanical needle insertion treatment approaches, the present approach provides more flexible control of therapeutic parameters, such as channel aspect ratio, and the side wall to bottom energy dose ratio.

For example, laser based drilling approaches tend to provide a side wall thermal damage zone that is similar to or larger than that at the bottom. However, the opposite dosage pattern (i.e., a larger coagulation zone at the bottom of the channels than on the sides) often provides more benefits for skin tightening than coagulation at the top of the channels. Reduced damage at the skin surface also helps to accelerate healing. With the present approach, this desirable dosage pattern (i.e., larger dose at channel bottoms than at channel sides) can be delivered.

Conventional needle electrodes that are mechanically inserted do not form empty channels in the tissue being treated. Healing response is improved by the presence of empty channels, so the ability of the present approach to provide such empty channels by ablation is a significant advantage relative to conventional needle electrode approaches.

DETAILED DESCRIPTION

In the present approach, channels are produced in skin (or any other kind of tissue) electrosurgically. More specifically, electrosurgical electrodes having a needle-like configuration can be employed to form channels in skin by electrically ablating tissue as the electrodes are inserted into the skin. Here and throughout this application, the term "ablation" refers to vaporization and removal of tissue. This electrosurgical system can produce patterns of channels in skin with predetermined depth and spacing. These channels are regions where tissue has been removed by ablation. The system can also adjust the extent of thermal coagulation in the surrounding tissue and at the edges of the channels. In addition, a coagulating waveform can be applied after partial or full insertion of the electrodes into the tissue in order to provide thermal treatment at the depth of the tissue, while sparing its surface.

Figure 1A:
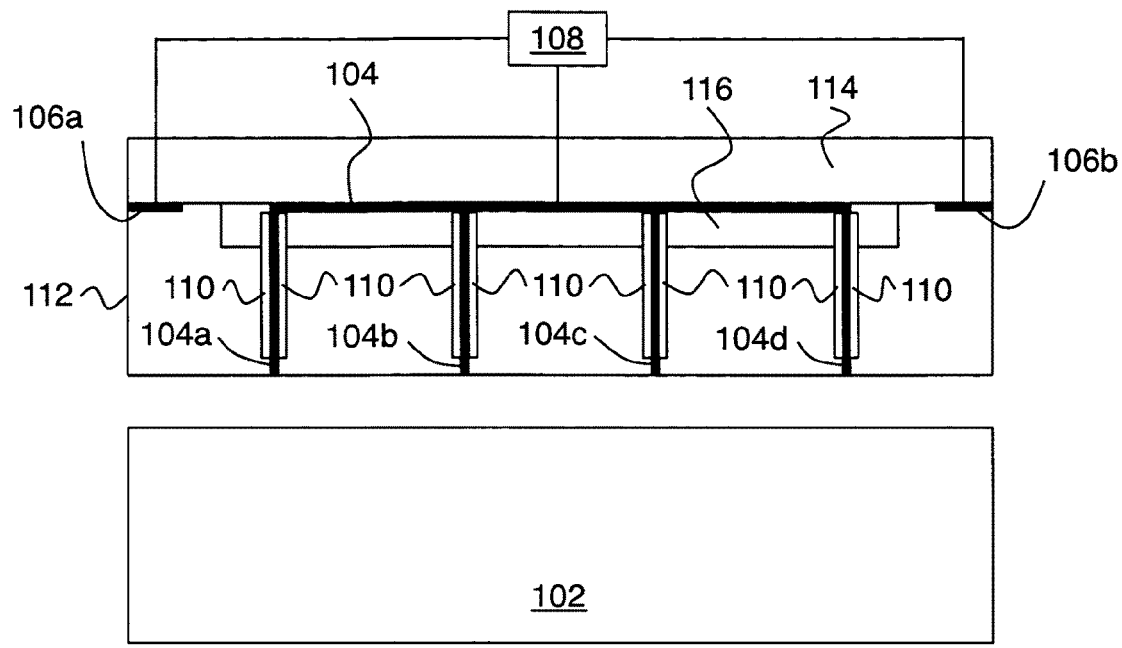
FIGS. 1a-e show an exemplary tissue treatment sequence making use of an embodiment of the invention.

An exemplary system is shown on FIG. 1a and includes the following components:
1) Power supply 108 delivering electrosurgical waveforms.
2) Array of microelectrodes 104 with electrode diameter preferably in the range of 25-250 micrometers, and electrode length preferably in the range of 0.1-2 mm.
3) Compressible or deflectable return electrode pad 112.

As shown in the example of FIGS. 1a-e, the electrosurgical waveforms can be applied between the active microelectrodes 104a-d, on the array and the large return electrode 106a-b placed on the surface of the body. The return electrode can be a metal film at the base of the array, and contact with the tissue being treated 102 (e.g., skin) can be achieved via a conductive fluid filling a foam or other compressible porous material 112 placed between the return electrode and the tissue surface.

This example includes some optional features of preferred embodiments. One such feature is the presence of insulator 110 on the sides of the protruding electrodes 104a-d. Another such feature is the disposition of a standoff plate 116 on electrode base 114. This standoff plate ensures that only the protruding parts of electrode array 104 can make contact with tissue 102.

Figure 1B:
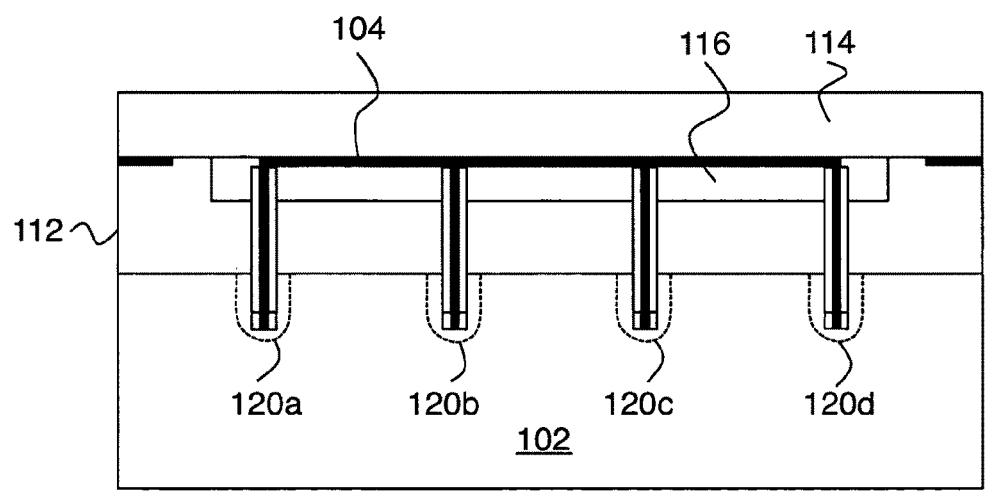
Figure 1C:
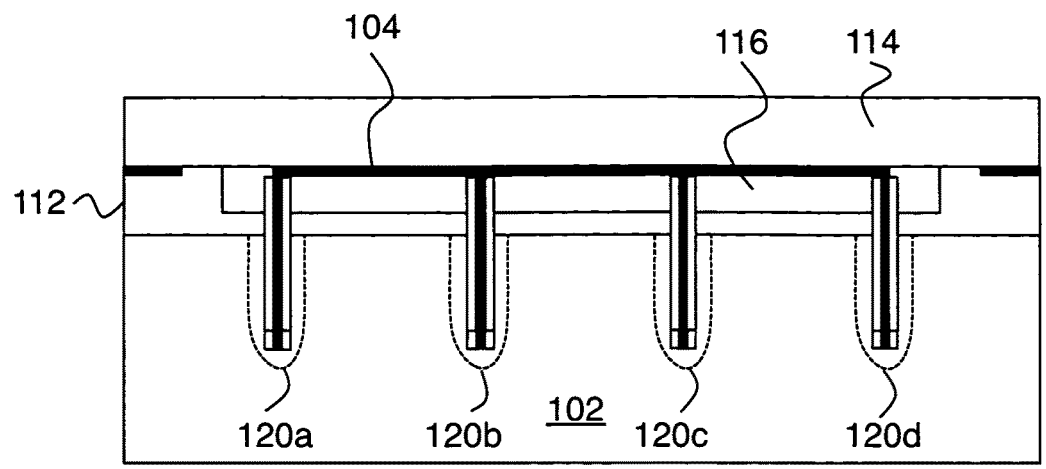
Figure 1D:
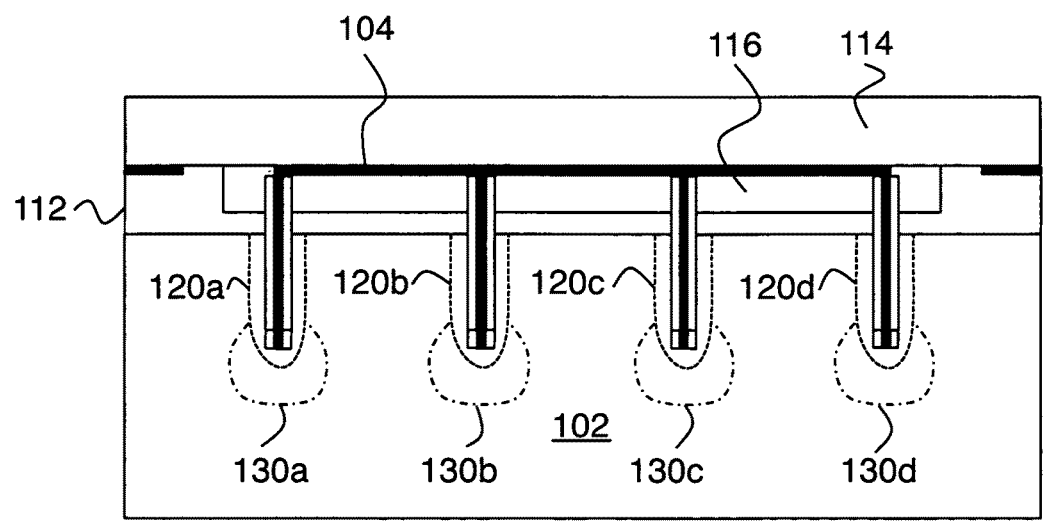
Figure 1E:
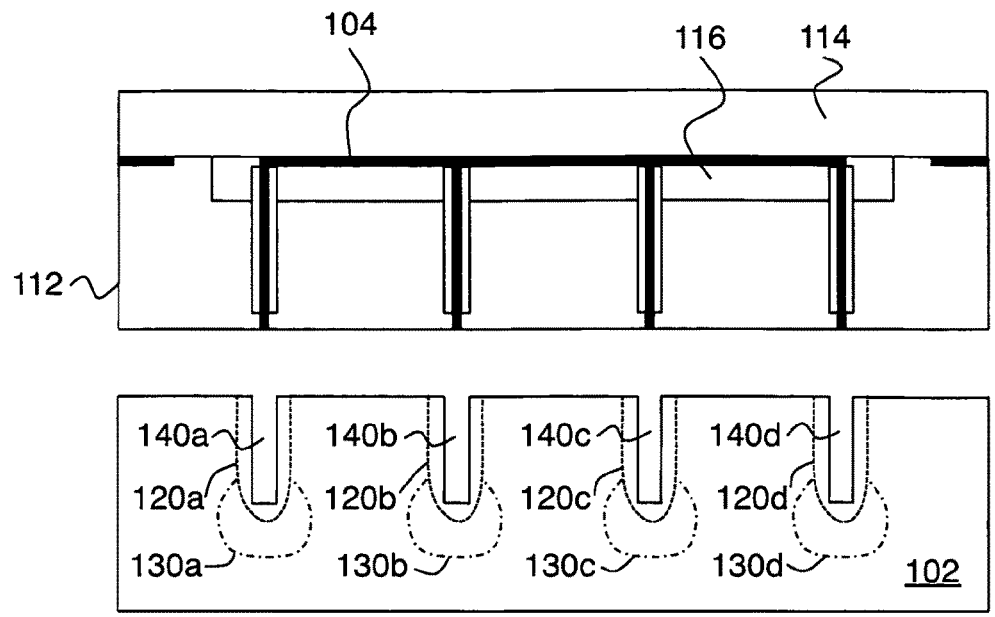

Upon application of pressure onto the array, the electrodes 104a-d will be pushed into the tissue 102, while the foam 112 is getting compressed, thus allowing the electrodes to move into the tissue (FIG. 1b). During insertion, the electrosurgical waveform is applied to the electrodes, producing plasma-mediated discharge predominantly at the tips of the electrodes. This discharge vaporizes the tissue in front of the electrode thus allowing for advancement. Additional energy can be deposited during or after the insertion for coagulation or thermal therapy of the skin. The resulting thermal damage zone at the channel sides is referenced as 120a-d. The example of FIGS. 1a-e shows an optional step of providing additional energy (FIG. 1d) after the electrodes are fully inserted (FIG. 1c). The resulting thermal damage zone at the channel bottoms is referenced as 130a-d. After the channels 140a-d are produced and tissue is heated, the array is pulled back, as shown in FIG. 1e. The procedure can be repeated to cover larger areas of skin surface.

The depth of the thermal damage zone 120a-d at the edges of the channels can be controlled by the structure of the electrode and by electrosurgical waveform. For very low damage, the waveforms should consist of bursts with duration shorter than 100 microseconds, so that the thermal diffusion zone will not exceed approximately 10 micrometers. Bursts should be applied with repetition rate not exceeding 1 kHz in order to allow tissue cooling between the bursts, and thus prevent heat accumulation. To achieve deeper penetration of heat, the waveform should have higher duty cycle to provide for deeper heat diffusion into tissue.

To minimize electric current, the side walls of the wire electrodes can be partially or completely covered with a thin layer of insulator 110, as shown in FIGS. 1a-e. The insulator should be thin enough in order to not interfere with advancement of the electrodes into tissue. Such insulation can also help reducing the effects of electrical stimulation of nerves and muscles in the treated tissue.

Even though electric current will be flowing from the microelectrodes to the return electrode on the surface through the bulk of tissue, due to enhancement of electric field around the tips of the electrodes, the thermal effects such as ablation and coagulation will be localized in these areas, and thus the damage to the bulk of the tissue between the microelectrodes can be minimized.

Figure 2:
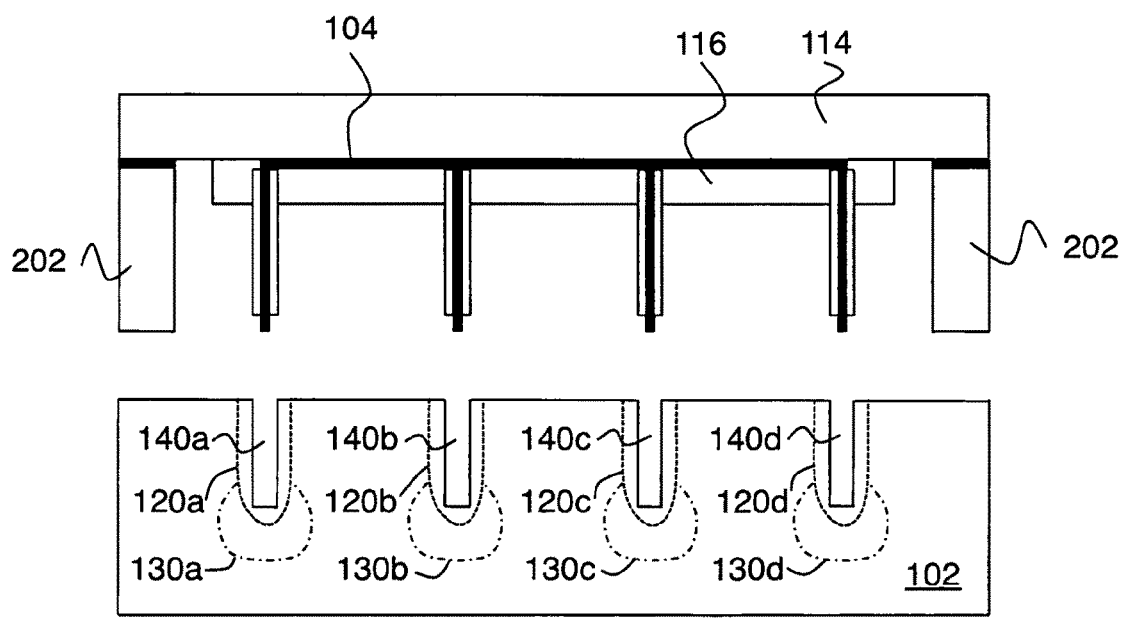
FIG. 2 shows an alternate embodiment of the invention.

Placement of the return pad electrode above the array can be employed to further minimize the current spread across the tissue, and reduce muscle and nerve stimulation. However, the return electrode can also be placed peripherally to the array (e.g., as in the example of FIG. 2), where compressible pad 202 laterally surrounds array 104 and effectively defines a peripheral return electrode, or even at remote part of the body.

Additional control of the extent of electric field penetration into tissue, and associated thermal effects can be provided by varying the length of the exposed fraction of the wire. The electric field decreases with distance from the electrode, with a characteristic penetration depth on the order of the exposed electrode size. Thus if only the tip of the wire is exposed, then penetration of electric field will be minimal—on the order of the wire diameter, and associated thermal damage will be relatively small. If a longer section of the wire will be exposed, then the electric field will expand accordingly.

There are several variations and modifications of this general approach. Preferably, the length of the protruding electrodes is in the range of 0.1-2 mm. Preferably, the diameter of the protruding electrodes is in the range of 0.03-0.5 mm, and is more preferably in the range of 0.05-0.1 mm.

The side walls of the electrodes in the array can be coated with insulator having a thickness that preferably does not exceed the electrode radius. Suitable insulators for this purpose include, but are not limited to glass, ceramics, and polymers. The protruding electrodes can be more or less completely insulated, as indicated above.

The return electrode can make contact to the surface of the body via a compressible material filled with conductive fluid. The electrosurgical waveform can include RF bursts, with burst duration preferably in the range from 10 to 1000 microseconds, and more preferably from 20 to 200 microseconds. The repetition rate of the bursts preferably does not exceed 10 kHz.

After the insertion is complete, an additional energy deposition can be applied to enhance tissue heating at the depth.

Any number of electrodes can be in the array: e.g., from 1×2 to 10×10 (one dimensional and 2-dimensional arrays).

In application of this system to skin treatment, the electrodes length should not exceed the thickness of skin.

The extent of tissue coagulation along the channel can be controlled by the ablative waveform. The extent of additional coagulation at the bottom of the array (i.e., at the bottom of the channels in the treated tissue) can be controlled by a second waveform that is activated after insertion is complete.

The waveform can vary with depth (i.e. with time during insertion), providing a continuous transition from the limited coagulation at the walls of the channel at the top surface of tissue to extended ablation/coagulation at the bottom of the channels.

The several electrodes in an array can be activated simultaneously and/or sequentially.

Figure 3:
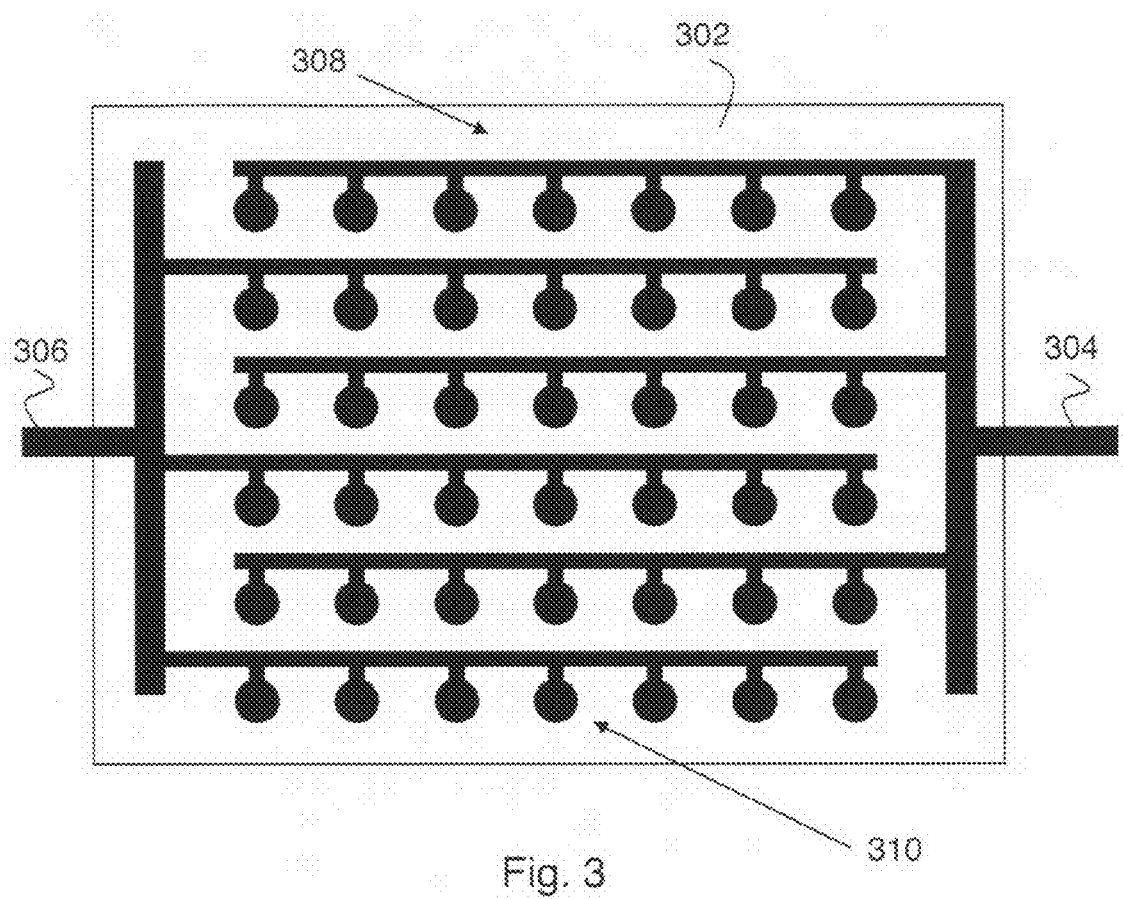
FIG. 3 shows a top view of an arrangement of active and return electrode suitable for use in embodiments of the invention.

An electrode array can include one or more return electrodes, e.g., as in the example of FIG. 3. In this example, an electrode array 302 has half of the electrodes 308 connected to the active side 304 of the power supply, and has the other half of the electrodes 310 connected to the return side 306 of the power supply. With part of the penetrating electrodes connected to the return, the return pad electrode may not be needed.

The present approach provides significant advantages. The use of variable waveforms during insertion provides flexibility for controlling and adjusting the extent of heating and coagulation at the sides and bottoms of the channels, while removing tissue inside the channels. Electrode length, diameter and array spacing can be selected according to the type/location of the skin and/or the skin condition being treated.

The invention claimed is:

1. Apparatus for electrosurgery of tissue, the apparatus comprising:
   an array of two or more protruding treatment electrodes adapted to be inserted into tissue and adapted to be connected to an electrical source,
   the array of two or more protruding treatment electrodes is configured to be energized by an electrosurgical waveform from the electrical source such that plasma-mediated interactions at the array of two or more protruding treatment electrodes ablate part of the tissue;
   one or more return electrodes; and
   a compressible pad configured to be disposed between the one or more return electrodes and the tissue during use, the array of two or more protruding treatment electrodes is adapted to project through the compressible pad when inserted into tissue.

2. The apparatus of claim 1, wherein the one or more return electrodes includes a return electrode at least partially surrounding the array of two or more protruding treatment electrodes.

3. The apparatus of claim 1, wherein the one or more return electrodes includes an array of two or more protruding return electrodes disposed on the array of two or more protruding treatment electrodes.

4. The apparatus of claim 1, wherein the array of two or more protruding treatment electrodes is at least one of one-dimensional and two-dimensional.

5. The apparatus of claim 1, wherein the apparatus is configured to provide skin treatment.

6. The apparatus of claim 1, wherein the electrical source is adapted to provide a pulse repetition rate of the electrosurgical waveform of 10 kHz or less.

7. The apparatus of claim 1, wherein the electrical source is adapted to provide a pulse duration of the electrosurgical waveform of 10 μs to 1000 μs.

8. The apparatus of claim 7, wherein the electrical source is adapted to provide a pulse duration of the electrosurgical waveform of 20 μs to 200 μs.

9. The apparatus of claim 1, wherein the electrical source is configured to energize the array of protruding treatment electrodes at least one of sequentially and simultaneously.

10. The apparatus of claim 1, further comprising an electrically insulating material coating the protruding treatment electrodes and defining a thickness, wherein each of the protruding treatment electrodes defines a radius, and wherein the thickness of the electrically insulating material is less than the radius of each of the protruding treatment electrodes.

* * * * *